United States Patent
Sharma et al.

(10) Patent No.: US 10,183,026 B2
(45) Date of Patent: Jan. 22, 2019

(54) METHOD OF ADJUVANT TREATMENT WITH CHLOROPHYLLIN CONTAINING THERAPEUTIC PREPARATION INCLUDING FOR RADIOPROTECTION OF NORMAL TISSUES DURING RADIATION THERAPY AND KIT THEREFOR

(71) Applicant: THE SECRETARY, DEPARTMENT OF ATOMIC ENERGY, Mumbai (IN)

(72) Inventors: Deepak Sharma, Mumbai (IN); Santosh Kumar Sandur, Mumbai (IN); Rahul Checker, Mumbai (IN); Raghavendra Shridhar Patwardhan, Mumbai (IN); Vikram Prakash Gota, Mumbai (IN); Jayakumar Sundarraj, Mumbai (IN); Preetha Sasi, Mumbai (IN); Subrata Chattopadhyay, Mumbai (IN)

(73) Assignee: THE SECRETARY, DEPARTMENT OF ATOMIC ENERGY, Mumbai (IN)

( * ) Notice: Subject to any disclaimer, the term of this patent is extended or adjusted under 35 U.S.C. 154(b) by 2 days.

(21) Appl. No.: 15/094,679

(22) Filed: Apr. 8, 2016

(65) Prior Publication Data
US 2017/0290843 A1 Oct. 12, 2017

(51) Int. Cl.
*A61K 31/555* (2006.01)
*A61N 5/10* (2006.01)

(52) U.S. Cl.
CPC .............. *A61K 31/555* (2013.01); *A61N 5/10* (2013.01)

(58) Field of Classification Search
CPC ................................ A61K 31/555; A61N 5/10
USPC ........................................................ 514/184
See application file for complete search history.

(56) References Cited

U.S. PATENT DOCUMENTS

2003/0105027 A1* 6/2003 Rosenbloom ............ A61K 8/42
424/94.4

FOREIGN PATENT DOCUMENTS

JP           H05194268     *   3/1993
WO     WO-2004064725 A2 * 8/2004 ............. A61K 8/602

OTHER PUBLICATIONS

Sharma et al. (Molecular Immunology (2007) vol. 44, pp. 347-359).*
Cope et al. (Photochem. Photobiol. Sci., (2006) vol. 5 pp. 499-507).*
Pimentel et al. (Biomarker Insights (2013), vol. 8, pp. 29-33).*
Williams et al. (Radiat Res. (2010) vol. 173, pp. 557-578).*
Guidance for Industry. Estimating the Maximum Safe starting dose in Initial clinical trials for therapeutics in adult healthy volunteeres . U.S. Department of Health and Human Services (FDA) Jul. 2005, pp. 1-30.*
Abraham et al. Mutation Research/Genetic Toxicology, (1994), vol. 322, pp. 209-212 (Year: 1994).*
Translation of JPH05194268 via Espacenet (Year: 2018).*
Gudkov A. V. et al.,"Radioprotection: smart games with death;" Journal of Clin Inves, 120:2270-2273, 2010.
Khan N. M. et al., "Pro-oxidants ameliorate radiation-induced apoptosis through activation of the calcium—ERK1/2-Nrf2 pathway" Free Radical Biology & Medicine, 51:115-128, 2011.
Takemura N. et al., "Blockade of TLR3 protects mice from lethal radiation-induced gastrointestinal syndrome;" Nature Communications, 5:3492, 2014.
Kouvaris J. R. et al., "Amifostine: The First Selective-Target and Broad-Spectrum Radioprotector," the Oncologist, 12:738-747, 2007.
Berbee M. et al., "γ-Tocotrienol Ameliorates Intestinal Radiation Injury and Reduces Vascular Oxidative Stress after Total-Body Irradiation by an HMG-CoA Reductase-Dependent Mechanism;" Radial Res, 171:596-605, 2009.
Landauer M. R. et al., "Genistein Treatment Protects Mice from Ionizing Radiation Injury" Journal of Applied Toxicology, 23:379-385, 2003.
Burdelya L. G. et al.,"An Agonist of Toll-Like Receptor 5 Has Radioprotective Activity in Mouse and Primate Models" Science, 320:226-230, 2008.
Visveder and Lindeman. "Cancer Stem Cells: Current Status and Evolving Complexities" Cell Stem Cell, 10:717-728, 2012.
Morales-Ramirez et al. "Effect of chlorophyllin on gamma ray induced micronuclei in polychromatic erythrocytes of murine peripheral blood determined by the ABC strategy" Mutation Research. Feb. 1996,(367(2):51-6).

(Continued)

*Primary Examiner* — Brandon J Fetterolf
*Assistant Examiner* — Taina D Matos Negron
(74) *Attorney, Agent, or Firm* — D'Ambrosio & Menon, PLLC; Usha Menon

(57) ABSTRACT

A method of increasing abundance of hematopoietic stem cells and progenitor cells and an adjuvant method of radiotherapy based treatment for radioprotection of the subject against γ-radiation toxicity and/or IR-induced death of cancer cells involving pharmaceutically effective dosages of chlorophyllin or a pharmaceutically acceptable salt thereof. The advancement is directed to selectively protect normal hematopoietic stem cells and/or sensitizes radio-resistant cancer cells to gamma radiation thereby lowering the risk of normal tissue radiation toxicity. The effective dose of the CHL formulation synergistically improves the outcome of radiotherapy for cancer when administered to the subject prior the radiotherapy for treating cancer. Also disclosed is kit having chlorophyllin containing therapeutic preparation for treating indications selected from reduction in hematopoietic stem cells and progenitor cells (HSPCs) and/or protection against whole body irradiation induced mortality.

3 Claims, 13 Drawing Sheets

(56) References Cited

OTHER PUBLICATIONS

Khan, N. et al. "Bilirubin augmentsradiationinjuryandleadstoincreasedinfection and mortality in mice Molecularmechanisms" Free Radical Biology & Medicine; Sep. 1, 2012;53(5):1152-1169.
Yin Li-ming et al., "Effects of sodium copper chlorophyllin on mesenchymal stem cell function in aplastic anemia mice" Chinese Journal Integr. Medicine, 19(5):360-366, 2013.
Singh, Vijay et al. "Medical Countermeasures for Radiation Exposure and Related Injuries: Characterization of Medicines, FDA-Approval Status and Inclusion Into the Strategic National Stockpile" Health Phys. 108(6):607-630; 2015.
Yoon, Sung-Il et al. "Structural Basis of TLR5-Flagellin Recognition and Signaling" www.sciencemag.org Science vol. 335 Feb. 17, 2012.

\* cited by examiner

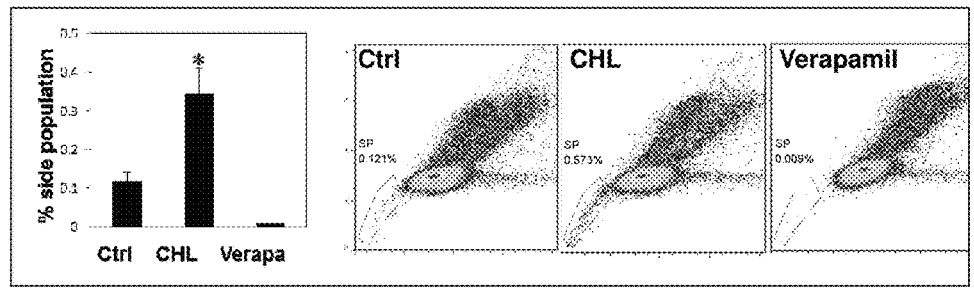
Fig 1A
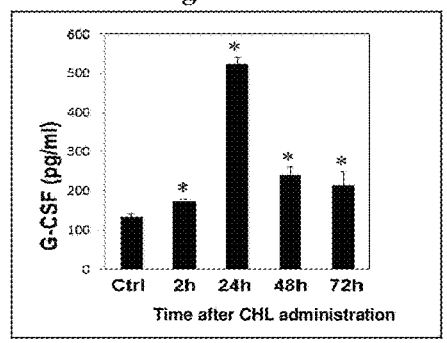
Fig 1B
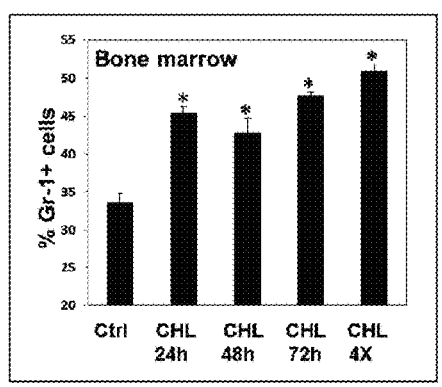 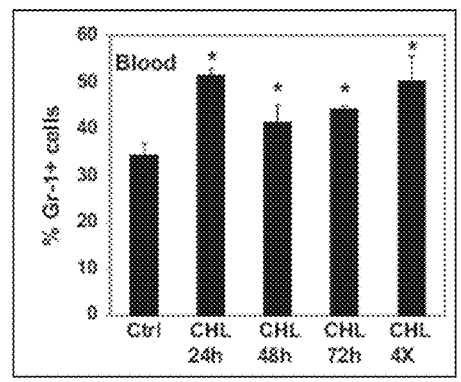
Fig 1C        Fig 1D

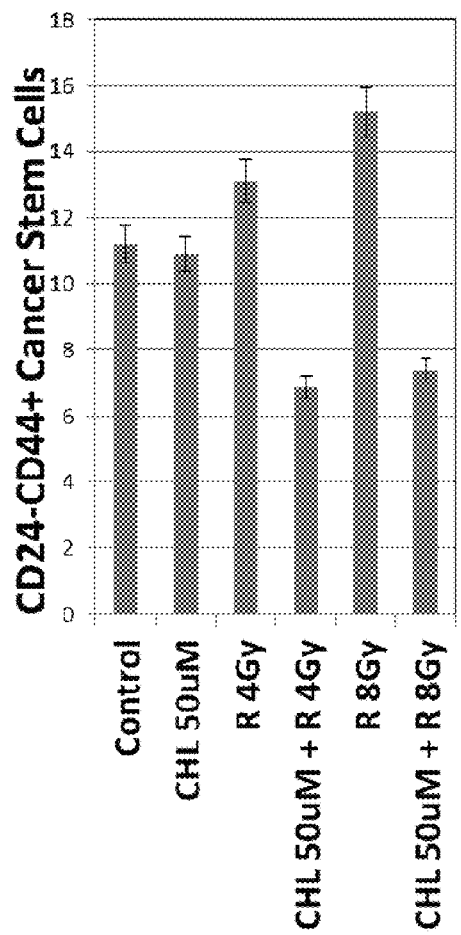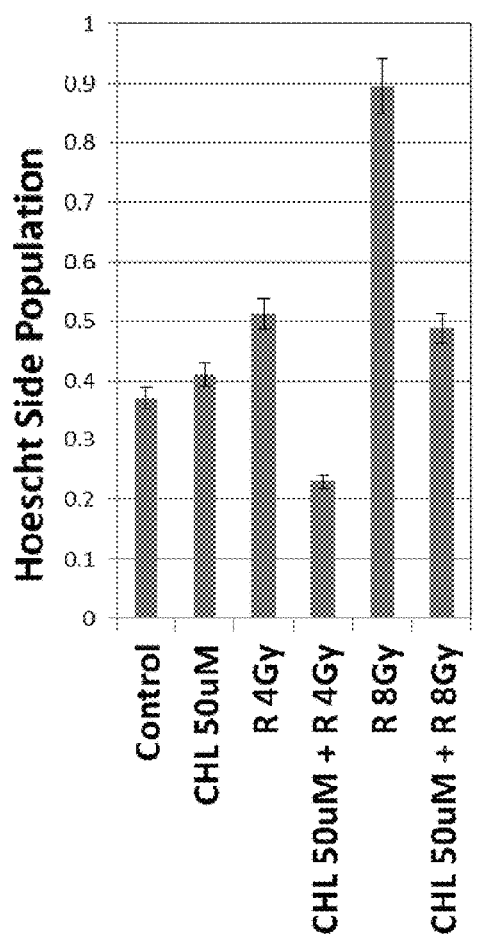
Fig. 7E                    Fig. 7F

METHOD OF ADJUVANT TREATMENT WITH CHLOROPHYLLIN CONTAINING THERAPEUTIC PREPARATION INCLUDING FOR RADIOPROTECTION OF NORMAL TISSUES DURING RADIATION THERAPY AND KIT THEREFOR

FIELD OF THE INVENTION

The present invention relates to an adjuvant treatment involving the same directed to physiological benefits by way of radioprotection against irradiation therapy such as increase in the abundance of hematopoietic stem cells and progenitor cells (HSPCs) when exposed to ionizing radiation. Importantly, the adjuvant therapy of the present advancement is directed to targeting cancer stem cells and sensitizing cancer cells including cancer stem cells to ionizing radiation thereby lowering the risk of normal tissue radiation toxicity. The advancement also provides for a therapeutic kit, more specifically to a kit having chlorophyllin containing formulation/preparation including a pharmaceutically effective amount of chlorophyllin or a pharmaceutically acceptable salt thereof.

BACKGROUND

The hematopoietic stem and progenitor cells (HSPCs) are the progenitor cells for all blood cells. The proliferation and differentiation of HSPCs give rise to the entire hematopoietic system. HSPCs are believed to be capable of self-renewal expanding their own population of stem cells and being pluripotent are capable of differentiating into any cell in the hematopoietic system. From this rare cell population, the entire mature hematopoietic system, comprising lymphocytes (B and T cells of the immune system) and myeloid cells (erythrocytes, megakaryocytes, granulocytes and macrophages) are formed. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides red blood cells, which act as oxygen carriers.

Various conditions in which HSPCs are depleted in the human body include leukemias, lymphomas, myelomas, different haematological disease such as phagocyte disorders, anaemia, viral diseases and external factors such as exposure to ionizing radiation. Hematopoietic stem and progenitor cells (HSPCs) are very sensitive to ionizing radiation and show massive apoptosis (~50%) at 1 Gy dose of γ-radiation. Exposure to higher doses of radiation induces severe depletion of HSPC and mitotic arrest. In order to reduce radiation toxicity to normal tissues during planned exposure, radiotherapy is delivered to tumours while minimizing the volume of normal tissue using different physical techniques. However, considering the anatomical location and unclear boundary between tumour and the surrounding normal tissue, normal tissue toxicity remains a major concern.

Several studies have been performed with objective to develop new and effective countermeasures to reduce, prevent or lower the risk of normal tissue radiation toxicity. Several drug targets such as free radicals, prosurvival transcription factors NF-κB and Nrf-2, cytokine receptors, toll-like receptors, and radical scavengers have been proposed. (Gudkov A. V. et al., J ClinInves, 120:2270-2273, 2010; Khan N. M. et al., Free RadicBiol Med, 51:115-128, 2011; and Tekmura N. et al., Nat Commun, 5:3492, 2014).

Amifostine was identified as a free radical scavenger and remains as the best drug tested as a radio-protector in clinic. It has been shown to prevent radiotoxicity in mucosal tissue in patients undergoing external radiotherapy for head and neck cancer, pelvis or brachytherapy for cervical cancers, and for patients undergoing radioiodine therapy (Kouvaris J. R. et al., Oncologist, 12:738-747, 2007). Several other molecules such as naphthoquinone, γ-tocotrienol, genestein, 3, 3'-diindolylmethane, and simvastatin which target cellular signaling machinery have been shown to exhibit potential radio-protective effects in experimental systems (Barbee M. et al., Radiat Res, 171:596-605, 2009 and Landauer M. R. et al., J ApplToxicol, 23:379-385, 2003). A flagellin-derived polypeptide CBLB502 which binds to toll-like receptor 5 (TLRS) and activates NF-κB in enterocytes and intestinal endothelial cells was discovered as both a radioprotector and a mitigator of radiation injury in mouse models (Burdelya L. G. et al., Science, 320:226-230, 2008). However, there is controversy over the radioprotective effects of these drugs towards tumour cells also. Moreover, until now, no radio-protective agent is clinically approved for prevention of radiation induced hematopoietic syndrome.

Cancer stem cells (CSCs) are resistant to chemotherapy and radiotherapy and are responsible for relapse of cancer in more than 50% of the patients. Recent observations suggest that it will be imperative to target all CSC subsets within the tumour to prevent relapse (Visveder and Lindeman. Cell Stem Cell, 10:717-728, 2012).

In spite of various methods known in the art to increase in vivo abundance of HSPCs, there still remains a need for new methods or compositions which can be used in conditions involving depletion of HSPCs. The present invention provides a pharmacological composition for specifically targeting and killing the cancer cells and particularly cancer stem cells while protecting the normal stem cells (HSPCs) during radiotherapy. The FDA-approved drugs, amifostine and palifermin are used for preventing the side effects of radiotherapy in cancer patients. However, these drugs per se have severe side effects and their protective action is not limited to the normal tissues.

Hence, there is a need to develop agents, which would specifically protect normal tissues, but not tumours and/or sensitize the tumour cells to radiation.

Chlorophyllin is a constituent of the over the counter drug Derifil and it falls under the class of GRAS (grossly recognized as safe) drugs. It has been earlier shown to scavenge free radicals derived from radiation. Chlorophyllin was also shown to act as an antioxidant and thereby prevent radiation-induced damage to biomolecules like DNA in cell free systems. Chlorophyllin was also shown to enhance the immune responses in mice. There are also reports that chlorophyllin inhibited radiation induced micronuclei induction and sister chromatid exchanges. However there are also reports showing that it did not prevent radiation induced DNA damage in mice (Mutat Res. 1996 February, (367(2): 51-6).

It is not obvious that an antioxidant should protect against radiation induced morbidity and mortality. Several antioxidants shown to reduce radiation induced micronuclei but there are no reports on these antioxidants protecting against radiation-induced mortality eg. Gallic acid, caffeic acid, vitamin C, vitamin E, glutathione, N-acetyl cysteine are all well-known antioxidants reported to reduce radiation induced micronuclei formation. However, only few of them offer protection against radiation induced mortality. Bilirubin is one of the most effective antioxidants but reported to enhance radiation induced mortality in mice (Free Radic Biol Med. 2012 Sep. 1; 53(5): 1152-69).

Several pro-oxidants like 1,4-Naphthoquinone have been shown to act as effective radioprotectors (Free Radic Biol Med. 2011 Jul. 1; 51(1):115-28). Granulocyte-Colony stimulation factor is an FDA approved radioprotector and it induces reactive oxygen species.

Effects of chlorophyllin on stem cells other than HSPC have been studied by Yin Li-ming et al. The study revealed the effect of sodium copper chlorophyllin on the proliferation, differentiation and immunomodulatory function of mesenchymal stem cells (MSCs) from mice with aplastic anaemia (Yin Li-ming et al., Chin J Integr. Med, 19(5):360-366, 2013). Yin Li-ming et al have shown the effect of a dose range of 25, 50 or 100 mg/kg body weight given to mice for 20 consecutive days after exposure of mice to 5 Gy dose of gamma irradiation. In their publication, there is no data on survivability of mice and the dose of radiation used is below the lethal dose. Increased MSC count cannot be correlated with increased survival after exposure to lethal dose of radiation. Further, the treatment regimen proposed by Yin-Li-Ming et al shows that the MSC can suppress immune responses, however, the regimen proposed by us shows more robust immune response (increased neutrophil counts) and faster recovery from radiation induced bone marrow aplasia. Yin et al have not investigated the effect of chlorophyllin on radiation induced hematopoietic syndrome. Thus, there are no reports until now on the radioprotecting effect of chlorophyllin on HSPCs and its therapeutic methodologies in relation to hematopoietic stem and progenitor cells (HSPCs) and radiotherapy for better therapeutic outcome.

Object of the Invention

It is thus the primary object of the present invention is to provide for adjuvant method of radiotherapy involving chlorophyllin containing therapeutic preparation as an adjuvant which would be capable of increasing abundance of hematopoietic stem cells and progenitor cells (HSPCs) and/or protects hematopoietic stem and progenitor cells (HSPCs) from gamma radiation-induced toxicity during radiotherapy for better therapeutic outcome.

Yet another object of the present invention is to provide for an adjuvant method of radiotherapy involving the said preparation for sensitizing human cancer cells to radiation induced death by inhibiting DNA repair leading to mitotic catastrophe.

Another object of the present invention is to provide a method of treatment involving the said therapeutic preparation in amounts of 100 mg/kg bw to 1000 mg/kg bw of mouse dose equivalent to 8.3 mg/kg bw to 83.33 mg/kg bw human dose with or without mortality.

A further object of the present invention is to provide for a method for enhancement of abundance of hematopoietic stem cells in the bone marrow, increasing G-CSF production leading to increased granulocyte output from bone marrow, increasing neutrophil count in the blood and transient cell cycle arrest in lineage negative cells.

Yet another object of the present invention is to provide for treating the conditions involving depletion of HSPCs, such conditions includes hematopoietic syndrome, immune suppression, aplasia, lymphopenia and lung injury.

It is still another object of the present invention to provide a kit having chlorophyllin containing therapeutic preparation in variety of dosage forms including selected from tablets, powders, lozenges, syrups, injectable solutions.

Another object of the present invention is to provide a kit having chlorophyllin containing therapeutic preparation, which is capable of increasing abundance of hematopoietic stem cells and progenitor cells (HSPCs), and/or protection against whole body irradiation induced mortality.

Another object of the present invention is to provide, a kit having chlorophyllin containing therapeutic preparation which sensitizes the cancer cells and cancer stem cells to gamma radiation.

Yet another object of the present invention is to provide a kit having chlorophyllin containing therapeutic preparation which selectively protects normal tissues and HSPCs and sensitizes the tumour cells and cancer stem cells simultaneously.

In yet another object, the present invention is to provide a kit having chlorophyllin containing therapeutic preparation suitable for prevention of radiation induced loss of bone marrow cellularity, lung damage and mortality.

SUMMARY OF THE INVENTION

Thus, according to the basic aspect of the present invention there is provided a method of increasing abundance of hematopoietic stem cells and progenitor cells comprising: administering the subject with pharmaceutically effective amount of chlorophyllin or a pharmaceutically acceptable salt thereof in amounts of 8.3 mg/kg bw to 83.33 mg/kg bw.

Another aspect of the present invention relates to the method wherein said pharmaceutically effective amount of chlorophyllin or a pharmaceutically acceptable salt thereof is administered for three consecutive days.

A further aspect of the present invention relates to the adjuvant method of radiotherapy based treatment for radioprotection of the subject against γ-radiation toxicity and/or IR-induced death of cancer cells comprising:
i) administering the subject with a pharmaceutically effective amount of chlorophyllin or a pharmaceutically acceptable salt thereof; followed by
ii) exposing the thus radioprotected subject to desired radiation for cancer treatment.

In another aspect, the present invention relates to the adjuvant method of radiotherapy treatment wherein said administering of dosage of said pharmaceutically effective amount of chlorophyllin or a pharmaceutically acceptable salt thereof is through intra peritoneal or oral methods.

In yet another aspect, the present invention relates to the adjuvant method of radiotherapy treatment comprising administering the said chlorophyllin or a pharmaceutically acceptable salt thereof in daily dosage in the level of 8.3 mg/kg bw to 83.33 mg/kg bw with or without antibiotic.

Yet another aspect of the present invention relates to the adjuvant method of radiotherapy treatment wherein the dosage level comprising selectively for radiation dose 6 to <8 Gy administering an amount of 8.3 mg/kg bw to 83.33 mg/kg bw through oral route for three consecutive days without antibiotic and for radiation dose 8 Gy and above administering an amount of 8.3 mg/kg bw to 83.33 mg/kg bw mg/kg bw through oral route for three consecutive days with antibiotic.

In another aspect, the present invention relates to the adjuvant method of radiotherapy treatment wherein the dosage level comprise selectively for radiation dose in the range of 6 to <8 Gy administering an amount 15 mg/kg bw to 41.66 mg/kg bw through oral route for three consecutive days without antibiotic and for radiation dose 8 Gy and above administering an amount of 15 mg/kg bw to 41.66 mg/kg bw mg/kg bw through oral route for three consecutive days with antibiotic.

In a further aspect, the present invention relates to the method wherein said pharmaceutically acceptable salt of chlorophyllin administered includes alkali magnesium or copper chlorophyllin such as sodium copper chlorophyllin, sodium or potassium magnesium chlorophyllin.

Another aspect of the present invention relates to the method carried out to selectively protect normal hematopoietic stem cells and/or sensitizing radio-resistant cancer cells to gamma radiation.

In yet another aspect, the present invention relates to the method carried out selectively for anyone or more of:
(a) increasing stem cell numbers in the bone marrow, granulocyte numbers and serum GCSF levels;
mitigating gamma radiation-induced toxicity to hematopoietic system and lungs;
b) for enhancement of abundance of hematopoietic stem cells in the bone marrow, increased G-CSF production leading to increased granulocyte output from bone marrow, increased neutrophil count in the blood and transient cell cycle arrest in lineage negative cells;
(c) sensitizing the cancer cells to gamma radiation;
(d) preventing γ-radiation induced hematopoietic syndrome and protecting cells in vivo against γ-radiation toxicity and also increased IR-induced death in human cancer cells;
(d) for sensitizing human cancer cells to radiation induced death by inhibiting DNA repair leading to mitotic catastrophe;
(f) for treating conditions involving depletion of HSPCs, such conditions includes hematopoietic syndrome, immune suppression, aplasia, lymphopenia and lung injury;
(g) for protecting normal hematopoietic stem cells and also sensitizing the radio-resistant breast cancer stem cells;
(h) for treating patients undergoing radiotherapy for treatment of breast and lung cancer;
(i) for transient cell cycle arrest in the lineage negative cells in the bone marrow and thereby enhancing the frequency of slow cycling hematopoietic stem cells enabling retention of stemness after exposure to radiation leading to faster recovery from radiation induced lymphopenia;
(j) to act as an antioxidant and immuno-stimulator and it has also been shown to scavenge radiation derived free radicals and reduce radiation induced DNA damage in normal tissue.

Yet in another aspect, the present invention relates to a kit for treating indications selected from reduction in hematopoietic stem cells and progenitor cells (HSPCs) and/or protection against whole body irradiation induced mortality comprising selectively:
chlorophyllin tablet containing chlorophyllin and/or its pharmaceutically acceptable salts as a therapeutic preparation in dosage form packaged in relation to radiation dependent dosage including selectively anyone or more of:
for radiation dose at 6 to 7.5 Gy variable dosages of said chlorophyllin dosage containing in the range of 8.3-83.33 mg/kg bw with directions for ready administration; and
for radiation dosage of 8 and above variable dosage of chlorophyllin tablets in the range of 8.3-83.33 mg/kg bw with antibiotic with directions for ready administration in combinations of one said chlorophyllin tablets and antibiotic.

In a still further aspect of the present invention is provided for a kit, wherein for ready administration in combinations of one said chlorophyllin dosage and antibiotic each combination dosage of said chlorophyllin dosage and antibiotic are packages side by side in said package.

A further aspect of the present invention relates to a kit, wherein each said package comprise tablet dosage for three consecutive days.

Yet another aspect of present invention relates to a kit wherein said pharmaceutically acceptable salt of chlorophyllin includes alkali magnesium or copper chlorophyllin such as sodium copper chlorophyllin, sodium or potassium magnesium chlorophyllin.

In another aspect, the present invention relates to a kit comprising pharmaceutically acceptable carriers, vehicles or diluents, said pharmaceutical carriers, vehicles and diluents including inert solid diluents or fillers, sterile aqueous solutions and various organic solvents, sweetening or flavourings, binders, excipients, dyes, emulsifying agents, suspending agents.

In a still further aspect, the present invention relates to a kit in variety of dosage forms including selected from tablets, powders, lozenges, syrups, injectable solutions.

BRIEF DESCRIPTION OF THE DRAWINGS

FIG. 1A represents effect of chlorophyllin on abundance of hematopoietic stem cells in the bone marrow as estimated by Hoechst side population assay.

FIG. 1B represents effect of chlorophyllin preparation on serum levels of G-CSF as a function of time.

FIGS. 1C & 1D show effect of chlorophyllin preparation on frequency of Gr-1+ granulocytes in the bone marrow and blood respectively.

FIG. 7E represents frequency of CD24-CD44+ CSCs in MDA-MB231 human breast cancer cells after treatment with CHL (50 µM) and exposure to 4 Gy or 8 Gy dose of radiation.

FIG. 7F represents frequency of CSCs as estimated by Hoechst side population assay in MDA-MB human breast cancer cells after treatment with CHL (50 µM) and exposure to 4 Gy or 8 Gy dose of radiation.

DETAILED DESCRIPTION

Figure 1E:
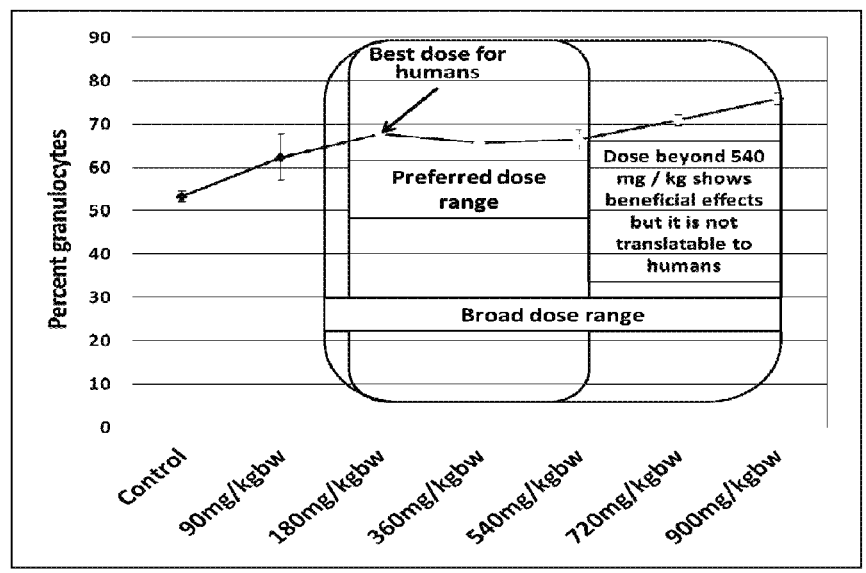
FIG. 1E illustrates the radioprotective dose of chlorophyllin in vivo by measuring % granulocytes.

The present advancement as above is thus directed to method of treatments involving the chlorophyllin containing therapeutic preparation and which would be capable of increasing abundance of hematopoietic stem cells and progenitor cells (HSPCs) and/or protect hematopoietic stem and progenitor cells (HSPCs) from gamma radiation-induced toxicity.

The advancement under the present invention demonstrates for the first time that therapeutic methods with chlorophyllin containing preparation could sensitize the cancer cells and cancer stem cells to gamma radiation, selectively protect normal tissues and HSPCs and sensitizes the tumour cells simultaneously, and resulting in prevention of radiation induced loss of bone marrow cellularity, lung damage and mortality.

According to another aspect of the present advancement there is provided for method of radiotherapy involving chlorophyllin containing therapeutic preparation as an adjuvant which would be capable of increasing abundance of hematopoietic stem cells and progenitor cells (HSPCs) and/or protects hematopoietic stem and progenitor cells (HSPCs) from gamma radiation-induced toxicity during radiotherapy for better therapeutic outcome.

According to yet further aspect the present advancement also directs to dosage based chlorophyllin containing preparation and selective therapeutic activity in increasing abundance of hematopoietic stem cells and progenitor cells (HSPCs) and/or protect hematopoietic stem and progenitor cells (HSPCs) from gamma radiation-induced toxicity, for sensitizing human cancer cells to radiation induced death by inhibiting DNA repair leading to mitotic catastrophe and for treating the conditions involving depletion of HSPCs, such conditions includes hematopoietic syndrome, immune suppression, aplasia, lymphopenia and lung injury.

The HSPCs exhibit high radio sensitivity and their ability to divide dramatically decreases following exposure to IR. It is by way of the present advancement that it is showed for the first time that administration of a CHL-containing formulation significantly enhanced the abundance of HSPC in vivo. Treatment with the formulation thus preserved the stemness of HSPC and prevented gamma radiation induced loss of proliferative potential in HSPC.

The radioprotective effect of chlorophyllin was found to be through enhancement of abundance of hematopoietic stem cells in the bone marrow, increased G-CSF production leading to increased granulocyte output from bone marrow, increased neutrophil count in the blood and transient cell cycle arrest in lineage negative cells.

Pharmacokinetic study showed that CHL-containing therapeutic preparation had a serum half-life of 141.8 min in mice. The formulation up-regulated anti-apoptotic genes and antioxidant machinery via activation of the pro-survival transcription factors Nrf-2 and NF-κB, and increased the survival and recovery of the bone marrow cells in mice exposed to WBI.

Prophylactic treatment of mice with the preparation significantly abrogated radiation induced normal tissue toxicity and mortality, while its therapeutic administration to mice after WBI significantly enhanced the hematopoietic recovery. The formulation also stimulated granulocyte production in bone marrow and increased the abundance of peripheral blood neutrophils by enhancing serum levels of granulocyte-colony stimulation factor (GCSF).

It was thus found surprisingly and unexpectedly that depletion of the abundance of the hematopoietic stem cells and progenitor cells (HSPCs) caused due to various conditions such as exposure to ionizing radiation can be reinstated or increased by administering a select pharmaceutical composition comprising chlorophyllin at selected dosage levels only.

The present invention relates to the antioxidant action of the said chlorophyllin preparation using cell-free, cellular, and animal systems along with the effects of chlorophyllin formulation on differentiation, proliferation, and radio sensitivity of cells from generative lymphoid organs which were not known before. Therapeutic effects of the said chlorophyllin formulation on cell survival, proliferation, differentiation, and apoptosis in generative lymphoid organs in normal mice and thus define its in vivo radioprotective action.

Importantly also the therapeutic preparation with the selected level of chlorophyllin did not show any toxicity in mice and rats up to an acute oral dose of 5 gm per Kg body weight and thus the said preparation and method of treatment involving the same was found to be safe (without side effects) in patients undergoing radiotherapy.

Following Table 1 summarizes the nature of treatment, dose of radiation, mouse dose of chlorophyllin* and expected outcome.

TABLE 1

| NATURE OF TREATMENT | RADIATION DOSE (GY) | BROAD DOSE OF CHLOROPHYLLIN & mode of administration | PREFERRED DOSE OF CHLOROPHYLLIN | OUTCOME |
| --- | --- | --- | --- | --- |
| Protection against whole body irradiation induced mortality in mice | 7.5 | 100-1000 mg/kg b.w. orally for three consecutive days (without antibiotics) | 180-500 mg/kg b.w. orally or three consecutive days (without antibiotics) | 100% protection against radiation induced mortality as monitored by 30 days survival |
| Protection against whole body irradiation induced mortality in mice | 8 | 100-1000 mg/kg b.w. orally for three consecutive days (with antibiotics) | 180-500 mg/kg b.w. orally for three consecutive days (with antibiotics) | 100% protection against radiation induced mortality as monitored by 30 days survival |
| Adjuvant for cancer radiotherapy of human breast cancer xenograft tumors in vivo in SCID mice | 6 | 100-1000 mg/kg b.w. orally for three consecutive days (without antibiotics) | 180-500 mg/kg b.w. orally for three consecutive days (without antibiotics) | Sensitization of human breast cancer xenograft tumors resulting in significant reduction in tumor after exposure to IR (50% reduction as compared to control mice bearing human xenograft human cancer cells) |

*Human equivalent dose is calculated by dividing the mouse dose with a factor (12) calculated from body surface area to weight ratio based on FDA Draft Guidelines.

Hence a dose of chlorophyllin without antibiotics equivalent to mouse dose of 100 to 1000 mg/kg body weight given daily by oral route for three consecutive days is the broad dose for protection against acute dose of radiation up to 7.5 Gy and is equivalent to human dose of 8.3 mg/kg bw to 83.33 mg/kg body weight.

A dose of chlorophyllin equivalent to mouse dose of 180 to 500 mg/kg body weight given daily by oral route for three consecutive days is the preferred dose for protection against acute dose of radiation up to 7.5 Gy and is equivalent to human dose of 15 mg/kg bw to 41.66 mg/kg body weight.

A dose of chlorophyllin equivalent to mouse dose of 180 mg/kg body weight given daily by oral route for three consecutive days is the most preferable dose without antibiotics for protection against acute dose of radiation up to 7.5 Gy and is equivalent to the human dose of 15 mg/kg body weight.

In certain cases of solid tumors, radiotherapy is used as a supplement to surgery and an acute local intra-operative dose of radiation 8.0 Gy is given to the tumour immediately after surgery which is higher than 7.5 Gy.

In these subjects receiving an acute dose of radiation more than 7.5 Gy, a dose of chlorophyllin equivalent to mouse dose of 100 to 1000 mg/kg body weight given daily by oral route along with antibiotics for three consecutive days is the broad dose, the equivalent human dose being 8.3 mg/kg bw to 83.33 mg/kg body weight.

Accordingly, a dose of chlorophyllin equivalent to mouse dose of 180 to 500 mg/kg body weight given daily by oral route along with antibiotics for three consecutive days is the preferred dose and is equivalent to the human dose 15 mg/kg bw to 41.66 mg/kg body weight.

In such subjects, a dose of chlorophyllin equivalent to mouse dose of 500 mg/kg body weight given daily by oral route along with antibiotics for three consecutive days is the most preferred dose which is equivalent to the human dose of 41.66 mg/kg body weight.

The above mentioned favourable, special and selective findings of the present advancement are further demonstrated by way of the following discussions on exemplary trials carried out involving the chlorophyllin containing preparation in accordance with the present invention as hereunder:

The details of the invention, its objects and advantages are explained hereunder in greater detail in relation to the following non-limiting accompanying figures and examples.

EXAMPLES

In vivo study was conducted using 8- to 9 weeks-old inbred BALB/c male mice, weighing approximately 20-25 g, reared in the animal house of Bhabha Atomic Research Centre were used. Mice were housed at constant temperature (23° C.) with a 12/12 hr light/dark cycle and were given mouse chow and water ad libitum.

In vitro study was conducted using MCF7 (breast cancer) and A549 (lung cancer) cell lines.

Example 1A: Chlorophyllin Formulation Enhanced Abundance of Hematopoietic Stem Cells in the Bone Marrow and Increased Granulocyte Production in BALB/c Mice 8- to 9 weeks-old inbred BALB/c male mice, weighing approximately 20-25 g, were grouped into untreated control and CHL treated groups.

CHL formulation dose and duration: 500 mg/Kg bw given orally for 3 consecutive days.

Side population analysis: The femur bones the above mentioned mice were dissected and the marrow was flushed out into cold Iscove's Modified Dulbecco's Medium (IMDM), 2% FBS using a 21-gauge needle. Nucleated cells were counted using Hemocytometer and trypan blue dye exclusion. Three million cells from each mouse were resuspended in pre-warmed (37° C.) DMEM without phenol red. Hoechst 33342 (5 mg/ml) was added and cells were incubated at 37° C. for 90 min with intermittent shaking. At the end of incubation, cells were washed with DMEM without phenol red and kept on ice and acquired on a flow cytometer within 2 h. Verapamil (100 μM concentration) treated bone marrow cells were used to identify the Hoechst side population in this assay.

Verapamil dose: 100 μM final concentration

Observation:

Mice treated with chlorophyllin formulation showed higher abundance (0.573%) (2-3 fold increase) of hematopoietic stem cells (FIG. 1A) than 0.121% in control groups (exposed to radiation only) and in Verapamil treated groups.

FIG. 1B shows the effect of chlorophyllin formulation in the above mentioned dose on serum levels of G-CSF in mice, exposed for 2, 24, 48 and 72 hrs with maximum rise after 24 hrs. The increase of serum G-CSF was correlated to the increase in the production of granulocytes (Gr-1+) in bone marrow and increased neutrophil frequency in the peripheral blood (FIGS. 1C & D).

Example 1B: Determination of Radioprotective Dose of CHL Formulation

Percent granulocytes are a biological marker for efficacy of chlorophyllin as a radioprotector in vivo. The increase in granulocytes in response to chlorophyllin treatment increases up to 180 mg/kg and then plateaus up to 540 mg/kg body weight dose. This is the preferred dose range. Although percentage of granulocytes increases at doses 720 and 900 mg/kg body weight, these doses are not preferred to be translated to humans. (FIG. 1E)

Example 2: Radioprotective Efficacy of Chlorophyllin Formulation in Irradiated BALB/c Mice Experimental animals 8- to 9 weeks-old inbred BALB/c male mice, weighing approximately 20-25 g, were treated with CHL formulation at the dose of 500 mg/Kg bw given orally for 3 consecutive days followed by whole body irradiation [using a 60Co γ-irradiator at a dose rate of 1 Gy/min (BhabhatronI II, Panacea, India)] of 7.5 Gy in one group and 6 Gy radiation to another group. Treated groups were compared to untreated control and mice treated only with CHL formulation at the given dose and mice with whole body irradiation without the CHL formulation.

7.5 Gy dose causes more severe bone marrow aplasia as compared to 6 Gy. Additionally, 7.5 Gy dose causes mortality in mice within 30 days due to severe damage to the immune system. 6 Gy dose causes immune suppression and bone marrow aplasia, but it does not lead to death of the mice within 30 days.

Hence survival % was assessed in the mice exposed to whole body radiation of 7.5 Gy and bone marrow cellularity was assessed in the group exposed to 6 Gy radiation following the method of side population analysis as explained in Example 1.

Figure 1F:
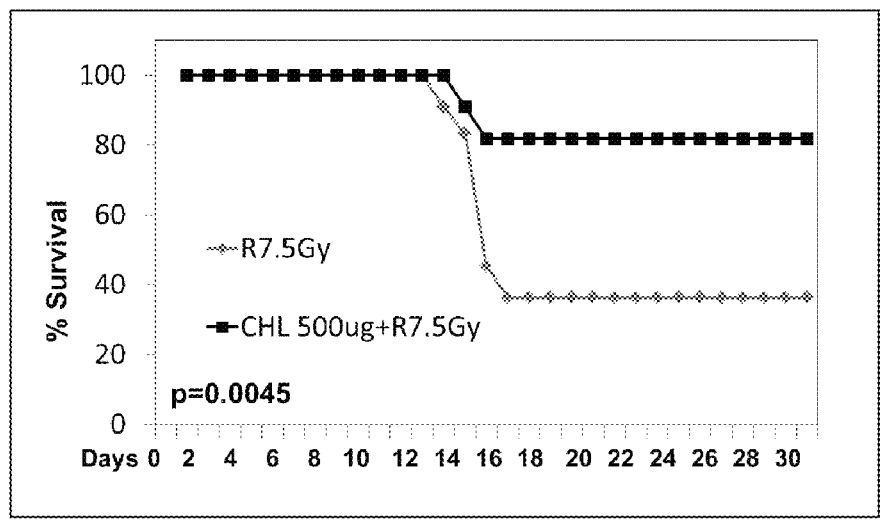
FIG. 1F shows the radioprotective efficacy of chlorophyllin against mortality in mice exposed to 7.5 Gy dose of whole body irradiation.
Figure 1G:
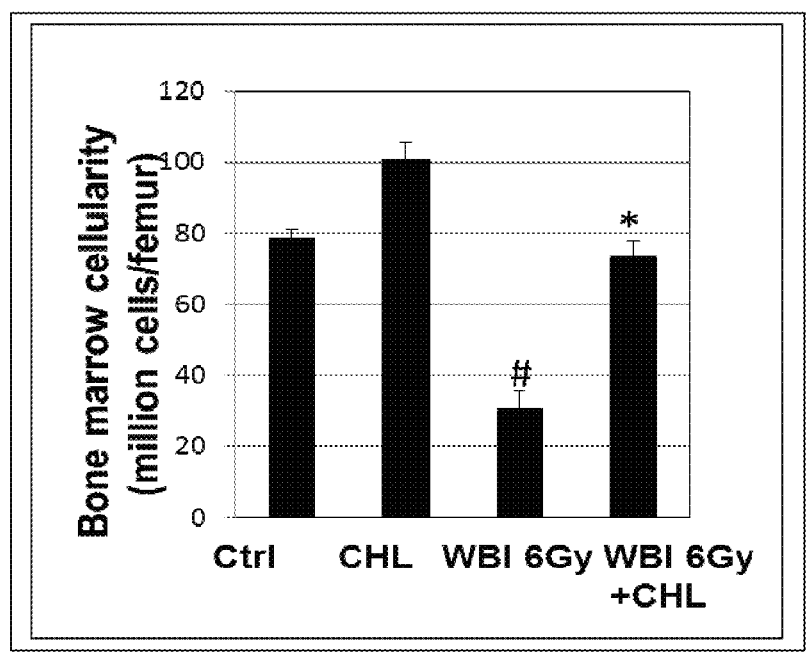
FIG. 1G represents effect of chlorophyllin on bone marrow cellularity in mice, which are exposed to 6 Gy whole body radiation.

Observation:

Chlorophyllin formulation at the given dose significantly protected mice against whole body irradiation (7.5 Gy) induced mortality (FIG. 1F). It enhanced the recovery from radiation (6 Gy) induced bone marrow aplasia in vivo (FIG. 1G).

Conclusion:

The HSPCs which are generally low in abundance, exhibit high radiosensitivity. As a result their ability to divide decreases dramatically following exposure to IR. It was found for the first time, that administration of the CHL formulation/agent in the specified dose significantly enhanced the abundance of HSPC in vivo. It induced a transient cell cycle arrest in lineage negative cells in the bone marrow. Treatment with the formulation preserved the stemness of HSPC and prevented gamma radiation induced loss of proliferative potential in HSPC. It significantly increased the number of colony forming units (CFUs) in bone marrow cells in vitro, of whole body irradiated mice.

Example 3: Chlorophyllin Enhanced Radiosensitivity and Slowing Down of DNA Repair in Cancer Cell Lines Exposed to 4 Gy Radiation To investigate the effect of chlorophyllin on radiosensitivity, evaluation of clonogenic survival and radiation induced DNA damage and repair in tumour cells by γH2AX foci formation assay were performed. The DNA repair kinetics of human lung cancer cells (A549) and breast cancer cells (MCF 7) and that were exposed to radiation after chlorophyllin treatment were also studied.

a) Clonogenic Survival Assay

A549 and MCF 7 cells (2000 cells for control, 4 Gy and 5000 cells for 8 Gy treatments) were plated overnight in 6 well plates followed by treatment with indicated concentrations of chlorophyllin (0, 10, 20, 50 or 100 μM) for 2 h and exposed to indicated doses of radiation. After radiation exposure plates were incubated at 37° C. in $CO_2$ incubator for 12 days for the development of colonies. After the colony formation, the plates were washed with PBS, fixed with methanol and stained with crystal violet. The colonies with more than 50 cells were counted and the survival fraction was calculated using the following formula: Survival fraction=No. of colonies/[no. of cells plated X (plating efficiency/100)], where plating efficiency is the ratio between the number of colonies developed to the number of cells plated in control.

Figure 2A:
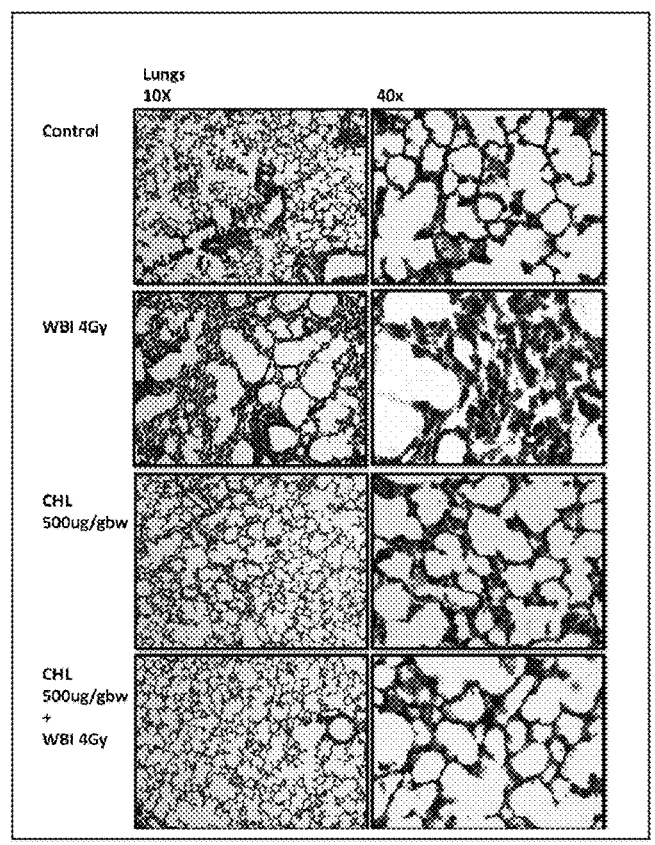
FIG. 2A Administration of CHL-formulation prevents gamma radiation (4 Gy)-induced injury to lung epithelial cells (cellular atypia).
Figure 2B:
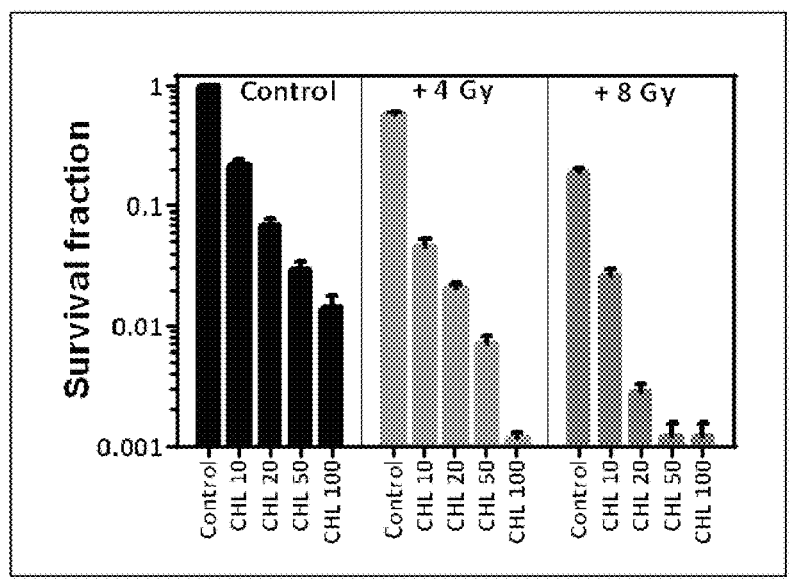
FIG. 2B represents the relative survival fraction of A549 human lung cancer cells after exposure to 4 Gy radiation in presence or absence of different concentrations of CHL (0, 10, 20, 50 or 100 µM).

Observation:

Chlorophyllin treatment significantly decreased the colony forming ability of A549 cells as compared to control and reduced gamma radiation (4 Gy)-induced injury to normal lung epithelia (cellular atypia) (FIG. 2A). Further, chlorophyllin was able to sensitize A549 cells to radiation induced loss of clonogenic capacity (FIG. 2B) evident from the gradually diminishing relative survival fraction of A549 human lung cancer cells after exposure to 4 Gy radiation in presence of different concentrations of CHL (0, 10, 20, 50 or 100 μM).

Figure 3A:
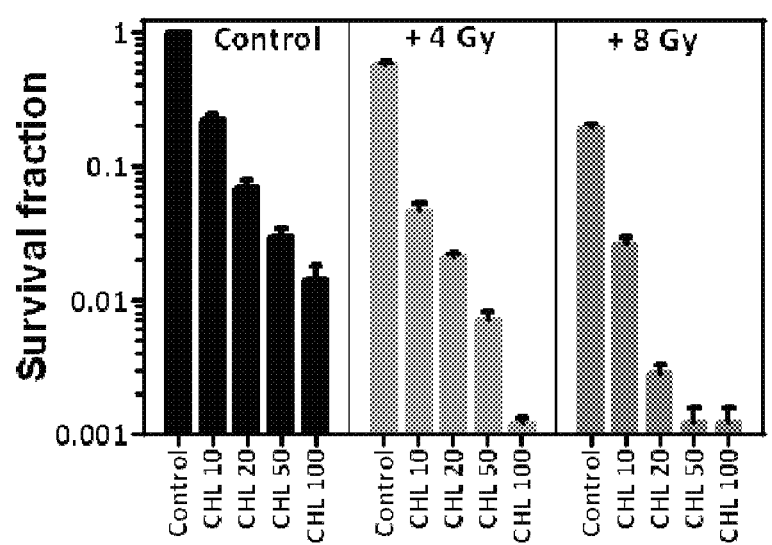
FIG. 3A represents relative survival fraction of MCF7 human breast cancer cells after exposure to 4 Gy radiation in presence or absence of different concentrations of CHL (0, 10, 20, 50 or 100 µM).

Chlorophyllin treatment significantly decreased the colony forming ability of MCF-7 cells as compared to control (FIG. 3A). Further, chlorophyllin significantly sensitized MCF-7 cells to radiation induced loss of clonogenic capacity (FIG. 3A) when compared to the non radiated chlorophylin treated cells.

b) γH2AX Foci Formation Assay

A549 cells and MCF ($3 \times 10^5$ cells) were grown on the coverslip, treated with 50 μM of chlorophyllin, followed by 4 Gy radiation exposure. At different time intervals after irradiation (either 15 min or 120 min), cells were fixed with 4% paraformaldehyde, permeabilized using Triton X-100, blocked with 5% bovine serum albumin and then treated with anti-γ-H2AX antibody. Then cells were stained with FITC labeled secondary antibody and visualized using fluorescence microscope. The average number of foci per cell was calculated after counting the foci from 100 cells per group.

Figure 2C:
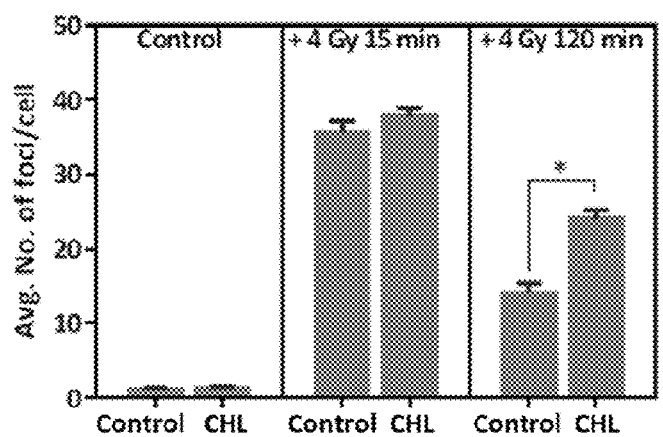
FIG. 2C represents number of ☐H2AX foci in A549 human lung cancer cells at different time intervals after exposure to 4 Gy radiation in presence or absence of CHL (50 µM).
Figure 2D:
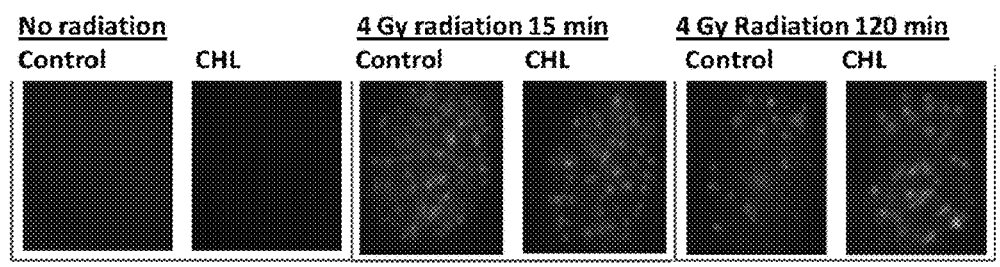
FIG. 2D represents images of ☐H2AX foci in A549 human lung cancer cells at different time intervals after exposure to 4 Gy radiation in presence or absence of CHL (50 µM).
Figure 3B:
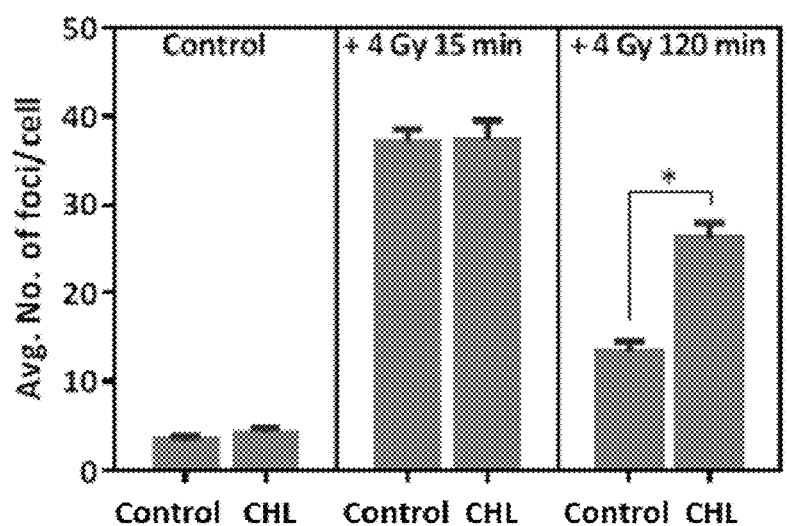
FIG. 3B represents number of ☐H2AX foci in MCF7 human breast cancer cells at different time intervals after exposure to 4 Gy radiation in presence or absence of CHL (50 µM).
Figure 3C:
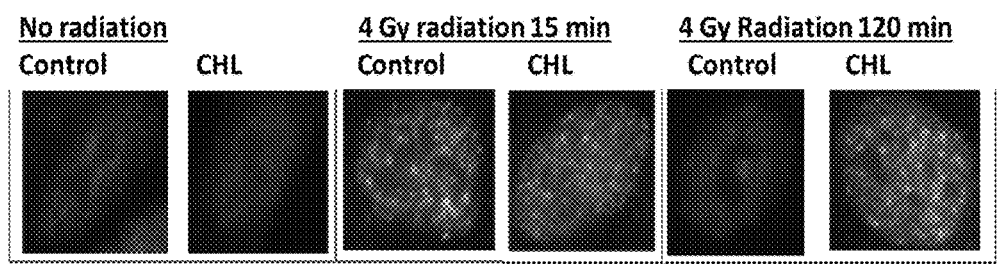
FIG. 3C represents images of ☐H2AX foci in MCF7 human breast cancer cells at different time intervals after exposure to 4 Gy radiation in presence or absence of CHL (50 µM).

Observation:

There was a significant increase in the number of γ-H2AX foci in cells 15 min after exposure to 4 Gy radiation. Chlorophyllin treatment did not have any effect on the number of γ-H2AX foci at this time point. However, at later time points of 120 minutes, the number of γ-H2AX foci in cells treated with chlorophyllin formulation was significantly higher (due to slowing down of DNA repair) than cells exposed to radiation alone (FIGS. 2C & D; FIGS. 3B & C).

Conclusion:

Chlorophyllin protected normal lung epithelia against radiation injury but enhanced radiosensitivity and slowed down DNA repair in A549 human lung cancer cells and also in MCF 7 breast cancer cells exposed to 4 Gy radiation. The persistence of DNA double strand breaks can lead to cell death and that has been reflected in decreased clonogenic survival of the cells which are treated with chlorophyllin prior to irradiation.

Example 4: Chlorophyllin Induced Mitotic Catastrophe in MCF-7 Human Breast Cancer Cells Exposed to 4 Gy or 8 Gy Radiation MCF-7 cells ($3 \times 10^5$ cells) were grown on the coverslip, treated with indicated concentrations of chlorophyllin (0, 10, 20, 50 or 100 μM) and exposed for 48 hrs to indicated doses of radiation (4 Gy and 8 Gy). After irradiation cells were fixed and stained with Hoechst and observed under fluorescence microscope. Cells with mitotic abnormalities have been counted for each group.

Figure 4A:
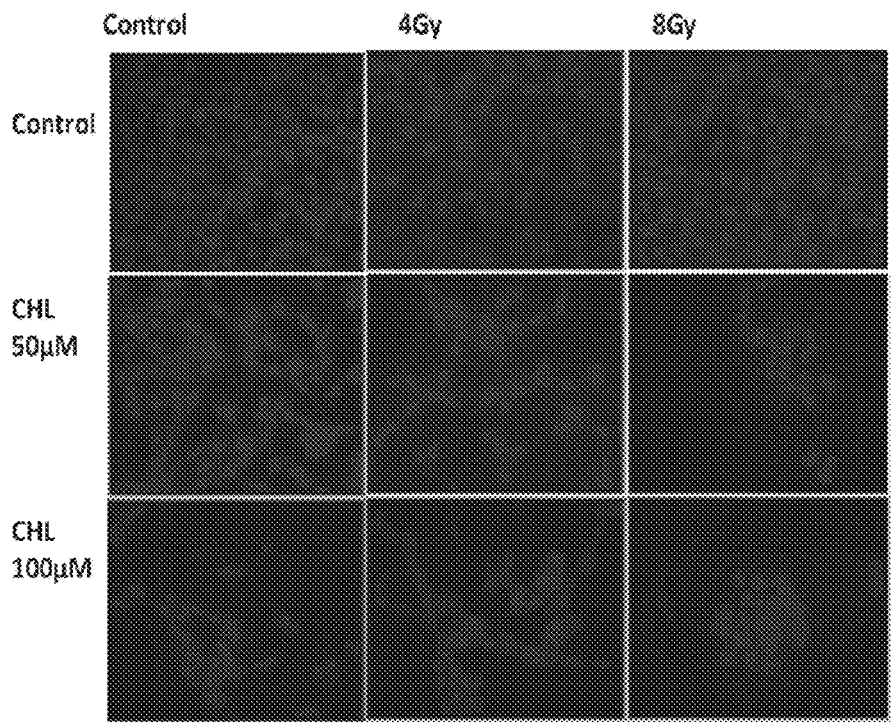
FIG. 4A represents microscopic images of Hoechst stained nuclei of MCF7 human breast cancer cells 48 h after exposure to 4 Gy or 8 Gy dose of radiation in presence or absence of different concentrations of CHL (0, 50 or 100 µM).
Figure 4B:
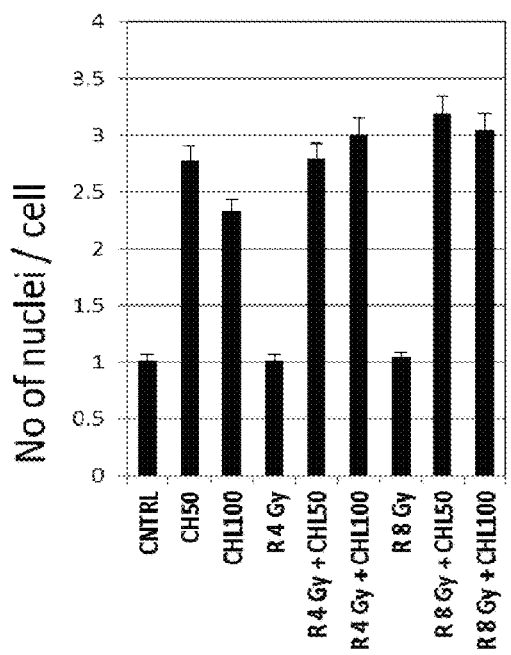
FIG. 4B represents average number of nuclei per cell in each group is shown in 4A FIG. 5 Relative levels of reactive oxygen species estimated by staining with DCFDA, Dihydroethidium or Dihydrorhodamine 123 at different time points after CHL treatment.

Observation:

It was observed that cells treated with chlorophyllin prior to radiation showed a pattern of mitotic catastrophe, including micronuclei and multinucleated giant cells (FIG. 4A). CHL treatment led to formation of multinucleated giant cells followed by reproductive death in breast cancer cells (FIG. 4B). Chlorophyllin enhanced the radiation toxicity in human breast cancer cells in vitro in a dose dependent manner.

Conclusion:

The chlorophyllin treated tumour cells were more sensitized to ionizing radiation resulting in reproductive death.

Example 5: Chlorophyllin Scavenged Radiation Induced Reactive Oxygen Species (ROS) in MCF-7 Cells In Vitro MCF-7 cells ($1 \times 10^5$) were stained with $H_2DCF$-DA (10 μM) Ex./Em. 485/535 nm or dihydroethidium (DHE 5 μM) 518/605 nm or DHR 123 (5 μM) 500/536 nm for 20 min and incubated with chlorophyllin (50 μM) or vehicle for indicated time intervals at 37° C. Cells were exposed to 4 Gy IR and fluorescence was monitored at respective wavelengths using BioTek Microplate Reader (Synergy).

Figure 5:
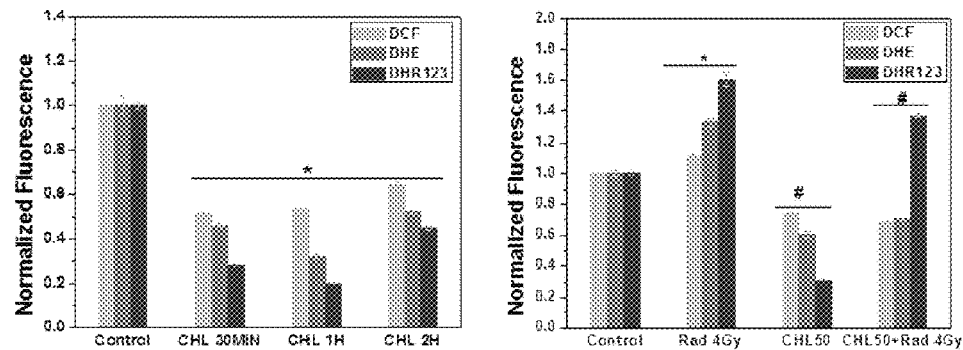

Observation:

It was found that exposure of cells to radiation led to a significant increase in the levels of reactive oxygen species as evinced from increase in the fluorescence of redox sensitive dyes like DCF, DHE and DHR123. Chlorophyllin treatment was able to scavenge background levels of free radicals in these cells and it also attenuated the radiation induced increase in intracellular ROS levels (FIG. 5).

Example 6: Chlorophyllin Enhanced Radiation Induced Decrease in the Frequency of Cancer Stem Cells (CSCS)

For cancer stem cell analysis, by Aldefluor assay, MCF7 cells and MDA MB231 cells were stained with either Aldefluor reagent or PE-CD244, APC-Cy7CD44, antibodies for 20 min on ice. The cells were washed and fixed with 1% paraformaldehyde for 20 min and stained with Hoechst 33342 (10 mg/ml) for 4 h. Isotype controls stained cells, single antibody stained cells, and fluorescence minus one (FMO) controls were used for compensation and gating. The cells were acquired on a flow Cytometer (Partec Cyflow) and analysed using FlowJo 7.6.5 (Treestar, Inc., Ashland) software.

Figure 6:
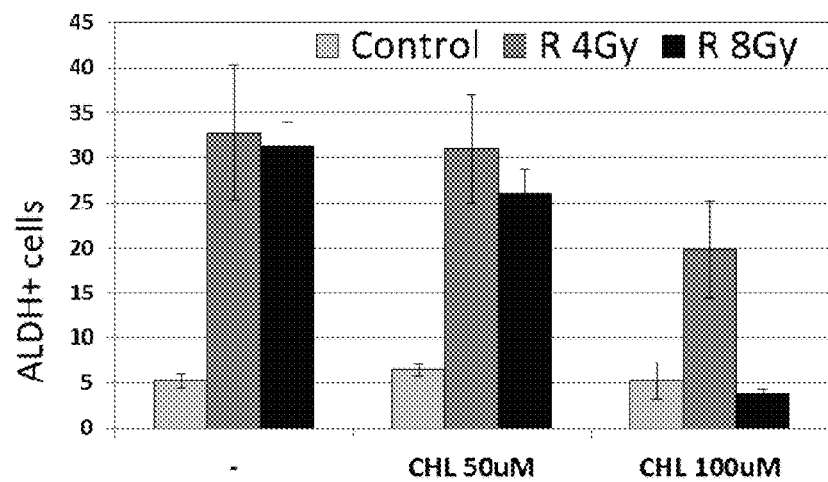
FIG. 6 represents the frequency of CSCs in MCF7 human breast cancer cells after treatment with CHL (50 and 100 µM) and exposure to 4 Gy or 8 Gy dose of radiation.

Observation:

i) Chlorophyllin enhanced radiation induced decrease in the frequency of cancer stem cells (CSCs) in MCF-7 breast cancer cells:

It was found that radiation increased the percentage of ALDH-positive cell population. However, treatment with chlorophyllin (100 μM) significantly attenuated the radiation induced increase in ALDH-positive cells (FIG. 6).

Figure 7A:
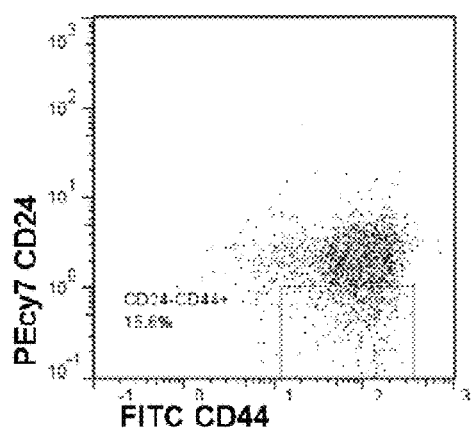
FIG. 7A represents the flow cytometric histogram for gating CD24-CD44+ CSCs in MCF7 human breast cancer cells.
Figure 7B:
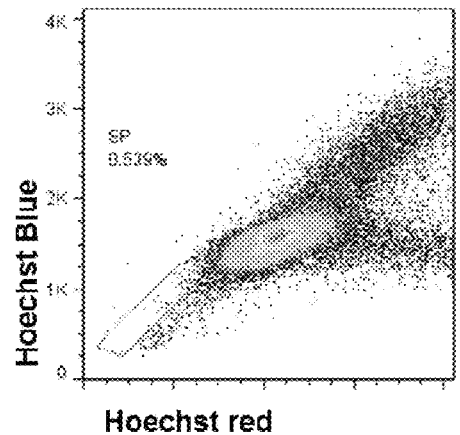
FIG. 7B represents the flow cytometric histogram for gating Hoechst side population for CSCs in MCF7 human breast cancer cells.
Figure 7C:
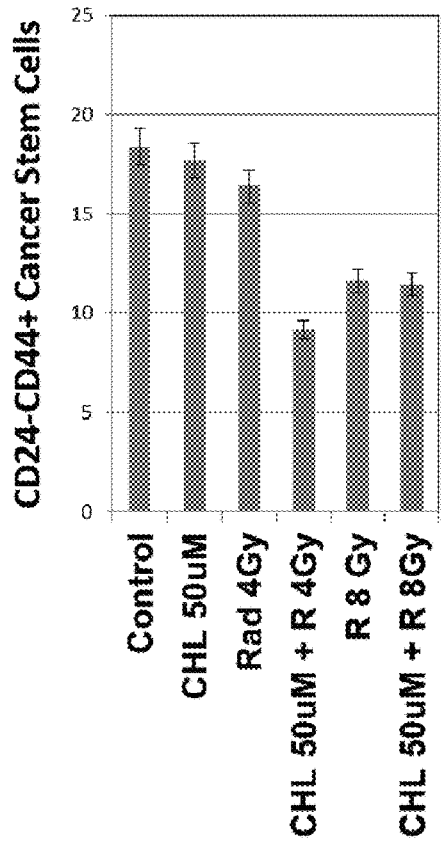
FIG. 7C represents frequency of CD24-CD44+ CSCs in MCF7 human breast cancer cells after treatment with CHL (50 µM) and exposure to 4 Gy or 8 Gy dose of radiation.
Figure 7D:
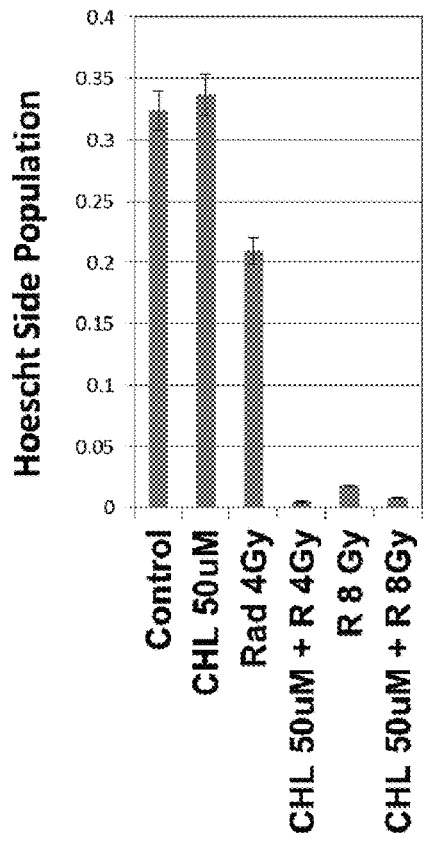
FIG. 7D represents frequency of CSCs as estimated by Hoechst side population assay in MCF7 human breast cancer cells after treatment with CHL (50 µM) and exposure to 4 Gy or 8 Gy dose of radiation.

The effect of radiation and chlorophyllin on CD24-CD44+ subpopulation of cancer stem cells were also studied. It was found that exposure of cells to 4 Gy or 8 Gy radiation led to a significant decrease in the percent of CD24-CD44+ cells. However, a combination of radiation and chlorophyllin was more effective than radiation or chlorophyllin alone in decreasing the percentage of cancer stem cells (FIGS. 7A & C). Similar results were obtained when CSCs were identified by their efflux of the fluorescent dye, Hoechst 33342 (FIGS. 7B & D).

ii) Chlorophyllin attenuated radiation induced increase in the frequency of cancer stem cells (CSCs) in MDA-MB 231 triple negative breast cancer cells:

It was observed that exposure of cells to 4 Gy or 8 Gy radiation led to a significant increase in the percent of CD24-CD44+ cells. Further, a combination of radiation and chlorophyllin (50 μM) was more effective than radiation or chlorophyllin alone in decreasing the percentage of cancer stem cells and similar results were obtained when CSCs were identified by their efflux of the fluorescent dye, Hoechst 33342 (FIGS. 7E & F).

Conclusion:

Cancer-initiating cells (CD24-CD44+ cells) which were more resistant to radiation did not maintain their survival advantage in presence of Chlorophyllin.

Example 7: In Vivo Radio Sensitization by Chlorophyllin on Human Breast Cancer Cells Using SCID Mice MCF-7 cells ($10\times10^6$ in 50 µl 1×PBS and 50 µl matrigel) were injected subcutaneously in foot pad of each mouse and tumors were monitored till they developed to measurable size. Mice were then treated with 500 mg/Kg bw chlorophyllin in PBS orally for three consecutive days. After last dose administration mice were locally exposed to IR 6 Gy (at the site of tumor) and subsequently monitored for 30 days for tumor growth and survival. Measurements of tumor were taken on alternate days using digital Vernier caliper and tumor volume was recorded. At the end of 30 days tumour mass was excised for further analysis.

Figure 8A:
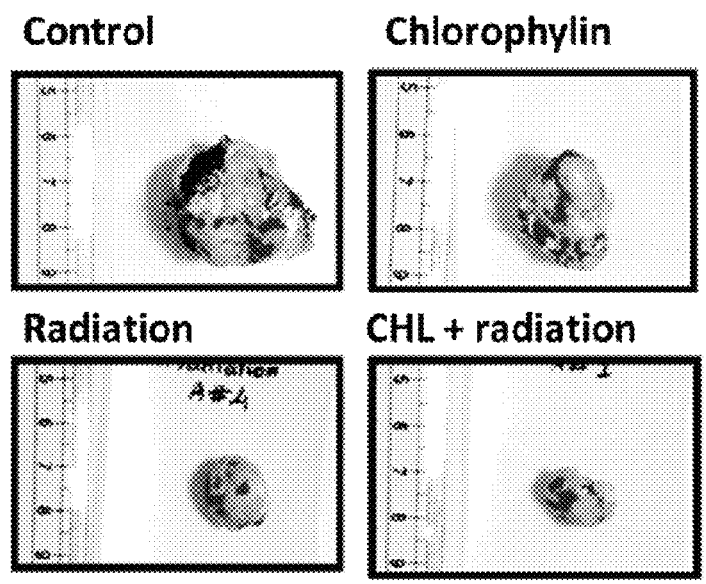
FIG. 8A represents the photographs of human breast cancer derived tumors isolated from SCID mice after treatment with CHL, radiation (6 Gy) or CHL+ radiation (6 Gy) as compared to control.
Figure 8B:
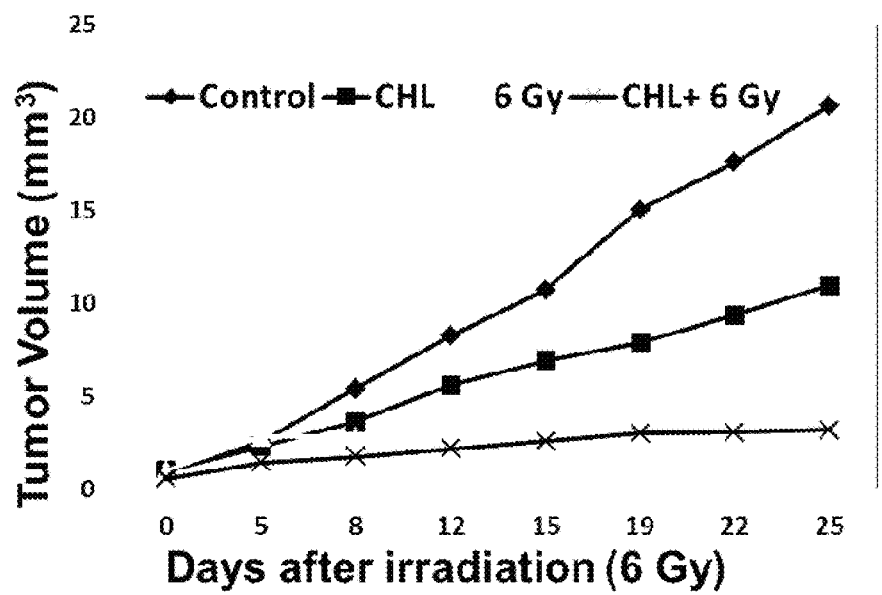
FIG. 8B represents the growth kinetics of human breast cancer derived tumors in SCID mice on different days after treatment with CHL, radiation (6 Gy) or CHL+ radiation (6 Gy) as compared to control.

Observation:

There was a significant decrease in the tumour volume of mice administered with chlorophyllin alone. Focal irradiation of the tumour to a dose of 6 Gy was more effective than chlorophyllin alone in preventing tumour growth. Further, a combination of chlorophyllin and radiation was most effective in preventing the growth of human breast cancer cells in SCID mice (FIGS. 8A & B).

Conclusion:

Chlorophyllin improved the outcome of radiotherapy in vivo. Since the radio-sensitizing effect of chlorophyllin was found to increase in a dose dependent manner in vitro, the highest radioprotective dose of chlorophyllin (500 mg/kg for three consecutive days) was chosen for the in vivo experiment. It was found that even at this high dose, chlorophyllin did not protect human breast cancer xenograft in vivo and did not offer survival advantage to tumors in presence of radiation.

Example 8: In Vivo Radioprotection by Chlorophyllin

To assess the in vivo radio protective efficacy of chlorophyllin, mice were given three consecutive oral administrations of: CHL formulation 1 containing chlorophyllin (500- mg/kg bw) and penicillin (10-50 mg/kg+ streptomycin 20-80 mg/kgbw) or CHL formulation 2 containing chlorophyllin (500 mg/kg bw) and tetracycline (20-80 mg/kgbw) at 24 h interval and were exposed to 8 Gy dose of whole body irradiation (which is used as a supplement to surgery during radiotherapy of cancer patients) 2 h after the last injection. Formulation 3 is chlorophyllin alone given at a dose of 500 mg/kg bw for three consecutive days with a gap of 24 h between each dose.

Figure 9:
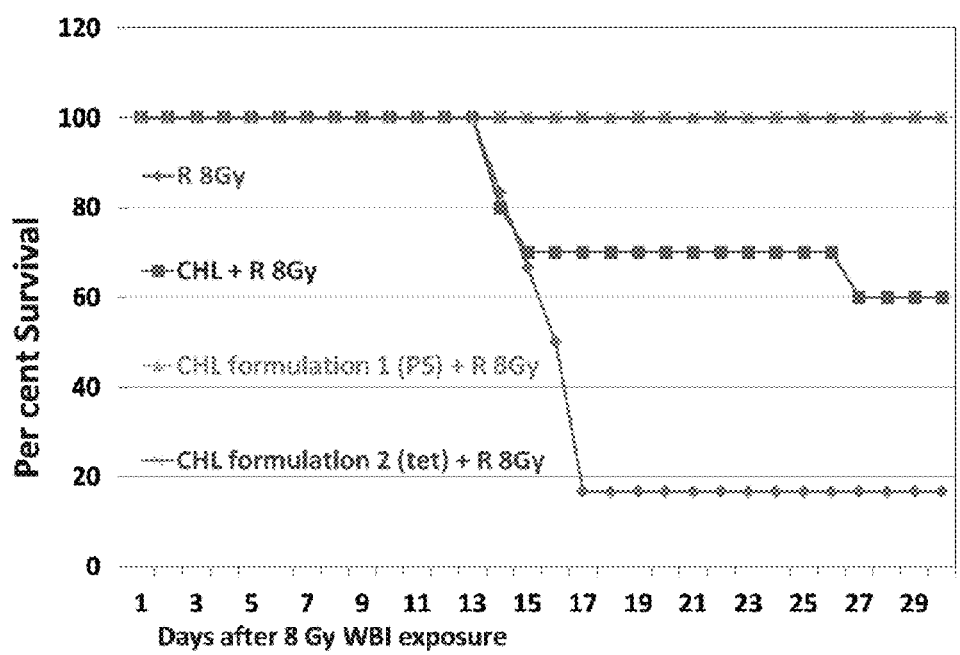
FIG. 9 represents percentage survival of mice injected with CHL formulation 1 (PS) and CHL formulation 2 (tet) for 4 consecutive days and exposed to 8 Gy dose of radiation at an interval of 24 h.

Observation:

30 days survival of mice following exposure to whole body radiation (WBI) was observed. 80% mice died within 17 days after exposure to 8 Gy WBI. However, chlorophyllin administration rescued all the mice against WBI-induced mortality (FIG. 9). The composition alone or in combination with said antibiotics, prevents the mortality of animals exposed to 8 Gy whole body irradiation. The group of mice treated by the composition/formulation with antibiotics show greater survivality of 100% than the mice treated with chlorophyllin alone.

The present advancement thus provides a chlorophyllin based formulation/agent for radioprotection of hematopoietic stem cells and progenitor cells by increasing the abundance when exposed to radiation and targeting cancer stem cells and sensitizing cancer cells including cancer stem cells to the ionizing radiation thereby lowering the risk of normal tissue radiation toxicity. Hence the above does demonstrate the advantages of the adjuvant therapy involving the chlorophyllin based formulation/agent for improving the outcome of radiotherapy for cancer.

In accordance with further aspect of the invention the dosage for the adjuvant therapy of the present advancement in relation to its radioprotective efficacy was further studied and the results are discussed and noted hereunder:

Example 9: Determination of Dose Regimen of CHL Formulation for Effective Radioprotection Against Ionizing Radiation Trials were conducted where chlorophyllin formulation ranging from 90 mg/kg bw to 2000 mg/kg body weight were administered to mice by oral gavage for three to four consecutive days at 24 h interval between doses. Alternatively, chlorophyllin was administered by intraperitoneal route (100 mg/kg body weight) for three consecutive days at 24 h interval. The mice were exposed to different doses of whole body irradiation (7.0 Gy, 7.5 Gy or 8 Gy) 2 h after last dose of chlorophyllin. The mice were monitored for changes in body weight and survival up to 30 days after WBI. The results of these trials are summarized in the table 2.

TABLE 2

Radioprotective efficacy of chlorophyllin dose regimen against 7.5 Gy IR

| Sr. No | Chlorophyllin dose | Route of administration | Number of days (24 h dosing) | Dose of whole body irradiation | Extent of protection offered to mice against radiation induced mortality |
|---|---|---|---|---|---|
| 1 | 90 mg/kg bw | Oral | 3 | 7.5 Gy | 66.6% |
| 2 | 180 mg/kg bw | Oral | 3 | 7.5 Gy | 100% |
| 3 | 500 mg/kg bw | Oral | 3 | 7.5 Gy | 70% |
| 4 | 2000 mg/kg bw | Oral | 4 | 7.0 Gy | 50% |
| 5 | 100 mg/kg bw | Intra peritoneal | 1 | 7.0 Gy | 30% |
| 6 | 100 mg/kg bw | Intra peritoneal | 4 | 7.0 Gy | 70% |

As would be apparent from the above results, an oral dose of 180 mg/kg bw of chlorophyllin for three consecutive days given at an interval of 24 h offered up to 100% protection against 7.5 Gy whole body irradiation induced mortality.

Another set of studies were carried out for optimal protection against mortality induced by higher dose of radiation (8.0 Gy whole body irradiation), where the dose of chlorophyllin required is 500 mg/kg body weight given by oral route daily for three consecutive days and it needs to be supplemented with antibiotics (either a combination of {1} penicillin and streptomycin or {2} tetracycline) for effective protection against 8 Gy whole body irradiation induced mortality. The results are noted hereunder:

TABLE 3

Radioprotective efficacy of chlorophyllin and antibiotic dose regimen against 8 Gy IR

| Sr. No | Chlorophyllin dose | Route of administration | Number of days (24 h dosing) | Dose of whole body irradiation | Extent of protection offered to mice against radiation induced mortality |
|---|---|---|---|---|---|
| 7 | 500 mg/kg bw + Penicillin + Streptomycin | Oral | 3 | 8.0 Gy | 100% |
| 8 | 500 mg/kg bw + Tetracycline | Oral | 3 | 8.0 Gy | 100% |
| 9 | 500 mg/kg bw | Oral | 3 | 8.0 Gy | 60% |

Radioprotective dose of 500 mg/kg CHL given daily orally for three consecutive days demonstrated that it did not protect human tumor cells against radiation in vivo. This data thus supplemented with in vitro experiments showing that different concentrations of chlorophyllin (10, 20, 50 or 100 µM) did not protect human breast cancer cells and human lung cancer cells against radiation. On the contrary, chlorophyllin enhanced the radiation induced cytotoxicity in human breast cancer cells and human lung cancer cells in vitro by inducing mitotic catastrophe and reproductive death.

Importantly, the above dose regimens using chlorophyllin are associated with increase in the production of Gr1+ neutrophils in the bone marrow and concomitant increase in the number of neutrophils in the blood demonstrating its radioprotective effect on the HPSCs.

The present advancement therefore for the first time has demonstrated that chlorophyllin enhanced radiation induced killing of human lung cancer cells and breast cancer cells by delaying the DNA repair leading to mitotic catastrophe and reproductive death. These findings were validated using human breast cancer xenograft model in vivo. Moreover, chlorophyllin protects the normal stem cells, enhances the proliferation of HPSCs when exposed to ionizing radiation. This differential action of chlorophyllin at a specific dose regime showing radioprotection to normal tissues and radiosensitization of cancer cells is surprisingly special and an unexpected advancement and provides for a much desired safe and effective adjuvant therapy to the radiotherapy of cancer.

We claim:

1. A method of radio sensitizing radioresistant cancer cells to gamma radiation by selectively inhibiting DNA repair leading to mitotic catastrophe in contrast to radio protection of normal stem cells consisting of oral administration of pharmaceutically effective amount of chlorophyllin or a pharmaceutically acceptable salt thereof at a dosage level of 41.66 mg/kg to 83.33 mg/kg body weight.

2. A method of radio sensitizing radioresistant cancer cells to gamma radiation according to claim 1, wherein pharmaceutically effective amount of chlorophyllin or a pharmaceutically acceptable salt thereof is administered orally at a dosage level of 41.66 mg/kg body weight for three consecutive days.

3. A method of radio sensitizing radioresistant cancer cells to gamma radiation according to claim 1, further comprising oral administration of pharmaceutically effective amount of chlorophyllin or a pharmaceutically acceptable salt thereof at a dosage level of 41.66 mg/kg to 83.33 mg/kg body weight for three consecutive days for enhanced radiation induced cytotoxicity in human breast cancer cells and/or human lung cancer cells by inducing mitotic catastrophe and reproductive death.

* * * * *